US011221335B2

(12) United States Patent
Tsuchiya (10) Patent No.: US 11,221,335 B2
(45) Date of Patent: Jan. 11, 2022

(54) HEAT-TREATED LIMULUS AMEBOCYTE LYSATES

(71) Applicant: Charles River Laboratories, Inc., Wilmington, MA (US)

(72) Inventor: Masakazu Tsuchiya, Mount Pleasant, SC (US)

(73) Assignee: Charles River Laboratories, Inc., Wilmington, MA (US)

( * ) Notice: Subject to any disclaimer, the term of this patent is extended or adjusted under 35 U.S.C. 154(b) by 0 days.

(21) Appl. No.: 16/675,978

(22) Filed: Nov. 6, 2019

(65) Prior Publication Data

US 2020/0217845 A1 Jul. 9, 2020

Related U.S. Application Data

(62) Division of application No. 14/228,993, filed on Mar. 28, 2014, now Pat. No. 10,473,664, which is a division of application No. 12/823,506, filed on Jun. 25, 2010, now Pat. No. 10,473,663.

(60) Provisional application No. 61/220,785, filed on Jun. 26, 2009.

(51) Int. Cl.
*G01N 33/579* (2006.01)

(52) U.S. Cl.
CPC ....... *G01N 33/579* (2013.01); *G01N 2400/24* (2013.01)

(58) Field of Classification Search
None
See application file for complete search history.

(56) References Cited

U.S. PATENT DOCUMENTS

| | | |
|---|---|---|
| 4,067,776 A | 1/1978 | Khan |
| 5,175,089 A | 12/1992 | Fine et al. |
| 5,266,461 A | 11/1993 | Tanaka |
| 5,310,657 A | 5/1994 | Berzofsky |
| 5,571,683 A | 11/1996 | Nakajima et al. |
| 5,616,557 A | 4/1997 | Tsuchiya et al. |
| 5,622,833 A | 4/1997 | Tsuchiya et al. |
| 5,681,710 A | 10/1997 | Tanaka et al. |
| 5,712,144 A | 1/1998 | Ding et al. |
| 5,716,834 A | 2/1998 | Ding et al. |
| 5,750,500 A | 5/1998 | Tsuchiya et al. |
| 5,858,706 A | 1/1999 | Ding et al. |
| 5,965,374 A | 10/1999 | Herbstritt et al. |
| 6,084,092 A | 7/2000 | Wakshull et al. |
| 6,294,321 B1 | 9/2001 | Wakshull et al. |
| 6,413,715 B2 | 7/2002 | Wakshull et al. |
| 6,630,310 B1 | 10/2003 | Wakshull et al. |
| 6,645,724 B1 | 11/2003 | Ding et al. |
| 6,719,973 B1 | 4/2004 | Ding et al. |
| 6,733,997 B1 | 5/2004 | Ding et al. |
| 6,849,426 B2 | 2/2005 | Chen et al. |
| 7,297,551 B2 | 11/2007 | Ding et al. |
| 7,329,538 B2 * | 2/2008 | Wainwright ......... G01N 33/579 435/288.7 |
| 7,335,515 B2 | 2/2008 | Tamura et al. |
| 10,473,663 B2 | 11/2019 | Tsuchiya |
| 10,473,664 B2 | 11/2019 | Tsuchiya |

FOREIGN PATENT DOCUMENTS

| | | |
|---|---|---|
| EP | 0569033 A2 | 11/1993 |
| EP | 2400302 A1 | 12/2011 |
| JP | 2004-109147 A | 4/2004 |
| JP | 2007-240397 A | 9/2007 |
| WO | WO-2010/095718 A1 | 8/2010 |
| WO | WO-2010/151751 A2 | 12/2010 |

OTHER PUBLICATIONS

Finkelman et al. (2005) "Detection of measurement of (1→3)-beta-D-glucan with Limulus amebocyte lysate based reagents", In: Toxicology of (1→3)-beta-D-glucans, pp. 179-197.*
Ascioglu, S. et al. (2002) Defining opportunistic invasive fungal infections in immunocompromised patients with cancer and hematopoietic stem cell transplants: an international consensus: *Clin. Infectious Diseases* 34:7-14.
Baek, L. et al. (1985) "Interaction between limulus amoebocyte lysate and soluble antigens from pseudomonas aeruginosa and *staphylococcus aureus* studied by quantitative immunoelectrophoresis" *J. of Clin. Microbiology* 22:229-237.
Cooper, J. et al. (1997) "The impact of non-endtoxin lal-reactive materials on limulus amoebocyte lysate analyses" *J. Pharma. Sci. Technol.* 51:2-6.
Finkelman et al. (2005) "Detection and Measurement of (1→3)-β-D-Glucan with Limulus Amebocyte Lysate-Based Reagents", In: "Toxicology of (1→3)-β-Glucans", 179-197.
Food and Drug Admin. (2004) "Class II special controls guidance document: serological assays for the detection of beta-glucan".
Graber, S. et al. (1982) "Direct evidence that bacterial lipopolysaccharides elevate cyclic GMP levels in rat fetal liver cells" *J. Bio. Chem.* 257:5414-5419.
Hossain, M. et al. (1997) "Comparison between wako-WB003 and fungitec G tests for detection of (1→3)-β-D-glucan in systemic mycosis" *J. of Clin. Lab. Analysis* 11:73-77.
Ikemura, K. et al. (1989) "False-positive result in limulus test caused by limulus amoebocyte lysate-reactive material in immunoglobulin products" *J. Clin. Microbiol.* 27(9):1965-1968.
International Search Report, International Patent Application No. PCT/US2010/039967, dated Mar. 15, 2011 (7 pages).
Iwanaga, S. et al. (1992) "Molecular mechanism of hemolymph clotting system in limulus" *Thromb. Res.* 68:1-32.
Kakinuma, A. et al. (1981) "Gelation of limulus amoebocyte lysate by an antitumor (1→3)-β-D-glucan" *Biocheck. Biophys. Res. Commun.* 101:434-439.
Kami, M. et al. (2000) "Computed tomographic scan of the chest, latex agglutination test and plasma (1→3)-β-D-glucan assay in early diagnosis on invasive pulmonary aspergillosis: A prospective study of 215 patients" *Haematologica* 85:745-752.

(Continued)

*Primary Examiner* — Vera Afremova
(74) *Attorney, Agent, or Firm* — Goodwin Procter LLP (57) ABSTRACT

The application provides heat-treated *Limulus* amebocyte lysates useful for detecting β-glucans.

14 Claims, 5 Drawing Sheets

(56) References Cited

OTHER PUBLICATIONS

Kawayama, T. et al. (2003) "High Concentration of (1→3)-β-D-glucan in BAL fluid in patients with acute eosinophilic pneumonia" *Chest J.* 123:1302-1307.
Kitagawa, T. et al. (1991) "Rapid method for preparing a β-glucan-specific sensitive fraction from limulus (tachypleus tridentatus) amoebocyte lysate" *J. Chromatography* 567:267-273.
Levin, J. et al. (1964) "The role of endotoxin in the extracellular coagulation of limulus blood" *Bull. Johns Hopkins Hosp.* 115:265-274.
Levin, J. et al. (1968) "Clottable protein in limulus: its localization and kinetics of its coagulation by endotoxin" *Thromb. Diath. Haemorrh.* 19:186-197.
Mitsutake, K. et al. (1996) "Enolase antigen, mannan antigen, can-tec antigen, and β-glucan in patients with candidemia" *J. Clin. Microbiology* 34(8):1918-1921.
Miyazaki, T. et al. (1995) "Plasma (1→3)-β-D-glucan and fungal antigenemia in patients with candidemia, aspergillosis, and cryptococcosis" *J. of Clin. Microbiology* 33(12):3115-3118.
Mori, T. et al. (1997) "Evaluation of plasma (1→3)-β-D-glucan measurement by the kinetic turbidimetric limulus test, for the clinical diagnosis of mycotic infections" *Eur. J. Clin. Chem. Clin. Biochem.* 35(7):553-560.
Morita, T. et al. (1981) "A New (1→3)-β-D-glucan-mediated coagulation pathway found in limulus amebocytes" *FEBS Lett.* 129:318-321.
Muta, T. et al. (1995) "Purified horshoe crab factor g" *J. Biol. Chem.* 270:892-897.
Nachum et al. "Inactivation of endotoxin by Limulus amoebocyte lysate" J Invertebr Pathol. Jul. 1978;32(1):51-8.
Nakao, A. et al. (1994) "Quantitative assay of (1→3)-β-D-glucan in culture media of candida albicans using the g-test" *European Surgical J.* 26:194-200.
Nakao, A. et al. (1997) "False-positive endotoxemia derives from gauze glucan after hepatectomy for hepatocellularcarcinoma with cirrhosis" *Hepato-Gastroenterology* 44:1413-1418.
Nakao, A. et al.(1997) "(1→3)-β-D-glucan determination in rat organs with limulus coagulation factor g" *Research in Experimental Medicine* 196:339-343.
Obayashi, T. et al. (1985) A new chromogenic endotoxin-specific assay using recombined limulus coagulation enzymes and its clinical applications *Clin. Chim. Acta* 149:55-65.
Obayashi, T. et al. (1992) "Determination of plasma (1→3)-β-D-glucan: a new diagnostic aid to deep mycosis" *J. of Medical and Veterinary Mycology* 30:275-280.
Obayashi, T. et al. (1995) "Plasma (1→3)-β-D-glucan measurement in diagnosis of invasive deep mycosis and fungal febrile episodes" *Lancet* 345:17-20.
Odabasi, Z. et al. (2004) "β-D-glucan as a diagnostic adjunct for invasive fungal infections: validation, cutoff development, and performance in patients with acute myelogenous leukemia and myelodysplastic syndrome" *Clin. Infect. Dis.* 39:199-205.
Official Action from Japanese Patent Application No. 2012-517765 dated Feb. 14, 2014 and English translation of same.
Ostrosky-Zeichner, L. et al. (2005) "Multicenter clinical evaluation of the (1→3) β-D-glucan assay as an aid to diagnosis of fungal infections in humans" *Clin. Infect. Dis.* 41:654-659.
Pazos, C. et al. (2005) "Contribution of (1→3)-β-D-glucan chromogenic assay to diagnosis and therapeutic monitoring of invasive aspergillosis in neutropenic adult patients: a comparison with serial screening for circulating galactomanna" *J. of Clin. Microbiology* 43(1):299-305.
Peason, F. et al. (1984) "Comparison of chemical analyses of hollow-fiber dialyzer extracts" *Artif. Organs* 8(3):291-298.
Supplementary European Search Report for Application No. EP 10792714, dated Jan. 14, 2013.
Tamura, H. et al. (1994) "Automated kinetic assay for endotoxin and (1→3)-β-D-glucan in human blood" *Clinica Chimica Acta* 226:109-112.
Tanaka, S. et al. (1991) "Activation of a limulus coagulation factor G by (1→3)-β-D-glucans" *Carbohydrate Research* 218:167-174.
The Fungatell product sheet description (2007), p. 1-2.
The Glucatell product sheet description (Mar. 2007), pp. 1-2.
Written Opinion, International Patent Application No. PCT/US2010/039967, dated Mar. 15, 2011 (6 pages).
Yoshida, M. et al. (1996) "Soluble (1→3)-β-D-glucan purified from candida albicans: biologic effects and distribution in blood and organs in rabbits" *J. of Lab. Clin. Medicine* 128(1):103-114.
Yoshida, M. et al. (1997) "Detection of plasma (1→3)-β-D-glucan in patients with fusarium, trichosporon, *Saccharomyces* and acremonium fungaemias" *J. of Medical & Veterinary Mycology* 35:371-374.
Yoshida, M. et al. (1997) "Pharmacokinetics, biological effects, and distribution of (1→3)-β-D-glucan in blood and organs in rabbits" *Mediators of Inflammation* 6:279-283.
U.S. Appl. No. 12/823,506, filed Jun. 25, 2010, U.S. Pat. No. 10,473,663, Masakazu Tsuchiya, Heat-Treated Limulus Amebocyte Lysates.
U.S. Appl. No. 14/228,993, filed Mar. 28, 2014, U.S. Pat. No. 10,473,664, Masakazu Tsuchiya, Heat-Treated Limulus Amebocyte Lysates.

* cited by examiner

Figure 1    Reactivity of crude LAL with β-glucan.

Figure 2    Reactivity of crude LAL with endotoxin (LPS).

Figure 3  Dose-response curve of β-glucan with LAL heated for different periods.

Figure 4  Dose-response curve of endotoxin with LAL heated for different periods.

Figure 5   Comparison of standard curves of β-glucan with and without of 200 EU/mL of US Reference Standard Endotoxin (ET).

Figure 6   Comparison of standard curves of β-glucan with and without of 500 ng/mL of endotoxin (ET) derived from *E. coli* O55:B5.

Figure 8  Arrhenius plots of endotoxin (Etx) reactivity and β-glucan (BG) reactivity.

HEAT-TREATED LIMULUS AMEBOCYTE LYSATES

REFERENCE TO RELATED APPLICATIONS

This application is a divisional of U.S. patent application Ser. No. 14/228,993, filed Mar. 28, 2014, now U.S. Pat. No. 10,473,664, which is a divisional of U.S. patent application Ser. No. 12/823,506, filed Jun. 25, 2010, now U.S. Pat. No. 10,473,663, which claims the benefit of U.S. Provisional Application No. 61/220,785, filed Jun. 26, 2009, the complete contents of each of which are incorporated by reference herein.

BACKGROUND OF THE INVENTION

*Limulus* Amebocyte Lysate (LAL) derived from the blood cells of the American horseshoe crabs react with endotoxin (Levin et al. (1964) *Bull. Johns Hopkins Hosp.* 115:265-274) or (1→3)-β-D-glucan (Kakinuma et al. (1981) *Biochem. Biophys. Res. Commun.* 101:434-439; Morita et al. (1981) *FEBS Lett.* 129:318-321), forming a gel. Endotoxin and β-glucan trigger two distinct LAL pathways, activation of either of which leads to gelation (Iwanaga et al. (1992) *Thromb. Res.* 68:1-32). Endotoxin is a cell wall component of Gram-negative bacteria, and is pyrogenic, mitogenic, and potentially lethally toxic. Accordingly, accurate and reliable detection of endotoxin is important for confirming the safety of parenteral drugs. LAL assays are the accepted standard for endotoxin detection (see, for example, the United States Pharmacopeia "Bacterial Endotoxins Test").

Because LAL reacts with either endotoxin or β-glucan, knowing which of the two activators is present in a sample is not necessarily straightforward. β-glucan is commonly found in fungi, yeast, algae, and plants, and causes false positives in Bacterial Endotoxin Tests. β-glucan contamination has been reported in parenteral drugs, such as blood products (Ikemura et al. (1989) *J. Clin. Microbiol.* 27(9): 1965-1968), and medical devices, such as hemodialyzers (Peason et al. (1984) *Artif. Organs* 8:291-298). The detection of β-glucan contamination in parenteral drugs and medical devices is useful to avoid unexpected rejection of a product that should not be rejected (Cooper et al. (1997) *J. Parenter. Sci. Technol.* 51:2-6).

β-glucan detection can also be used on human blood samples to assist in the diagnosis of deep mycosis (Obayashi et al. (1995) *Lancet* 345:17-20; Mori et al. (1997) *Eur. J. Clin. Chem. Clin. Biochem.* 35:553-560; Odabasi et al. (2004) *Clin. Infect. Dis.* 39:199-205; Ostrosky-Zeichner et al, (2005) *Clin. Infect. Dis.* 41:654-659). The FDA and the Japanese government have each approved such assays as clinical diagnostic methods.

The challenge has been to develop reliable, cost-effective assays for β-glucan detection that can distinguish the presence of β-glucan from the presence of endotoxin. Several processes for increasing the β-glucan specificity of LAL have been reported.

Fractionation methods (Obayashi et al. (1985) *Clin. Chim. Acta* 149:55-65; Kitagawa et al. (1991) *J. Chromatography* 567:267-273; and U.S. Pat. No. 5,681,710) are based on removing the endotoxin sensitive factor ("Factor C") from LAL by column chromatography, or by separation steps between solid absorbents and LAL. The column chromatography and separation steps must be performed aseptically. Thus, these systems can require expensive instruments and significant efforts to prevent contamination of the system with endotoxin or β-glucan.

Another approach suppresses endotoxin activity in samples using endotoxin-neutralizing peptides (U.S. Pat. Nos. 5,616,557; 5,622,833; and 5,750,500). Efforts to suppress endotoxin activity can be affected by high amounts of endotoxin, and require the addition of anti-endotoxin substances that may be expensive and contaminated with endotoxin or β-glucan.

U.S. Pat. No. 5,571,683 adds an endotoxin neutralizing peptide to a β-glucan assay with LAL. This method requires the purification of an endotoxin neutralizing peptide from the blood of horseshoe crabs. The purification can be expensive, and avoiding contamination with endotoxin and β-glucan during the purification can be difficult.

Similarly, U.S. Pat. No. 5,266,461 adds an antibody against Factor C. This method requires preparation, synthesis and purification of antibody, again adding expense and the risk of contamination with endotoxin or β-glucan during the purification process.

Thus, despite the efforts over the past two decades to develop β-glucan assays, there remains a need for a simple method for preparing LAL with a reduced sensitivity to endotoxin.

SUMMARY OF THE INVENTION

It has been reported that heating lysates from Asian horseshoe crabs (*Tachypleus tridentatus*) to temperatures above 40° C. quickly inactivated the β-glucan-sensitive factor ("Factor G") (Muta et al. (1995) *J. Biol. Chem.* 270:892-897). It has now been discovered that the same is not true of lysates harvested from the American horseshoe crab, *Limulus polyphemus*. Rather, *Limulus* Factor G appears to be comparatively heat-stable. Specifically, when LAL is heated to a temperature above 40° C., sensitivity of the LAL to endotoxin is lost more quickly than sensitivity of the LAL to β-glucan. Exploiting the differential heat-sensitivity of the endotoxin and β-glucan pathways in LAL permits the preparation of lysates with reduced reactivity to endotoxin, while retaining reactivity to (1→3)-β-D-glucan.

Accordingly, in one aspect, the invention relates to methods of preparing a *Limulus* amebocyte lysate (LAL) with increased specificity for (1→3)-β-D-glucan. The methods include heating the LAL to a temperature above 40° C. to reduce reactivity to an endotoxin. The invention also relates to methods of preparing a *Limulus* amebocyte lysate with reduced sensitivity to an endotoxin. The methods include heating the LAL to reduce Factor C activity in the lysate while retaining reactivity to (1→3)-β-D-glucan. The heating conditions can be selected to provide a lysate in which reactivity to endotoxin is only mildly reduced, or in which endotoxin reactivity is substantially eliminated, affording a lysate that is (1→3)-β-D-glucan-specific.

Importantly, if excessive heating (such as 56° C. for 30 minutes) is avoided, reactivity of the LAL to (1→3)-β-D-glucan can be retained. For example, the resulting lysate may remain sensitive to concentrations of carboxymethylated pachyman (a (1→3)-β-D-glucan) of 100 ng/mL; 10 ng/mL; 1 ng/mL; 100 pg/mL; 10 pg/mL; 1 pg/mL; or 0.1 pg/mL.

In some embodiments, the (1→3)-β-D-glucan reactivity of the LAL is reduced by a factor of not more than 1,000 (i.e. retaining at least 0.1% of the original reactivity), not more than 100 (retaining at least 1% of the original reactivity), not more than 50 (retaining at least 2% of the original reactivity), not more than 10 (retaining at least 10% of the original reactivity), not more than 5 (retaining at least 20% of the original reactivity), or not more than 2 (retaining at least 50% of the original reactivity).

The reduction in endotoxin reactivity should exceed reductions in reactivity to (1→3)-β-D-glucan. If a substantial reduction in endotoxin reactivity is desired, the reduction can be by a factor of at least 10 (i.e. retaining no more than 10% of the original reactivity), at least 50 (retaining no more than 2% of the original reactivity), at least 100 (retaining no more than 1% of the original reactivity), at least 500 (retaining no more than 0.2% of the original reactivity), at least 1,000 (retaining no more than 0.1% of the original reactivity), at least 5,000 (retaining no more than 0.02% of the original reactivity), at least 10,000 (retaining no more than 0.01% of the original reactivity), at least 100,000 (retaining no more than 0.001% of the original reactivity), or at least 1,000,000 (retaining no more than 0.0001% of the original reactivity).

Typically the methods involve heating the LAL to between 40° C. and 80° C., although at higher temperatures (particularly at or above 56° C.), heating times should be correspondingly brief to avoid also rendering the LAL insensitive to (1→3)-β-D-glucan. For example, at temperatures above 56° C. the heating time is preferably less than one minute. In contrast, depending on the desired degree of reduction in endotoxin reactivity, if the temperature is no more than 45° C., heating times exceeding 40 minutes may be used.

In certain circumstances, the LAL is heated for at least a minimum time to achieve a desired reduction in endotoxin reactivity. For example, the heating time may be selected to exceed $t_{A1}$ hours, where $t_{A1} = 0.825 * 2.718^{(56340/(T+273))}/(9.54*10^{76})$, where T is the temperature in ° C., in some cases achieving an approximately 1000-fold reduction in endotoxin reactivity. Alternatively, the heating time may be selected to exceed $t_{A2}$ hours, where $t_{A2} = 1.65 * 2.718^{(56340/(T+273))}/(9.54*10^{76})$, in some cases achieving an approximately 1,000,000-fold reduction in endotoxin reactivity. More generally, the LAL is optionally heated for at least $t_A$ hours, where $t_A = K * 0.275 * 2.718^{(56340/(T+273))}/(9.54*10^{76})$; K may be, for example, 0.5, 1.0, 1.5, 2.0, 2.5, 3.0, 3.5, 4.0, 4.5, 5.0, 5.5, 6.0, 6.5, 7.0, 7.5, 8.0, or more, depending on the desired magnitude of endotoxin reactivity inactivation.

In the methods described above, the LAL heating time optionally is no more than $t_{B1}$ hours, where $t_{B1} = 0.353 * 2.718^{(76510/(T+273))}/(2.20*10^{103})$, where T is the temperature in ° C., in some cases retaining at least approximately 10% of reactivity to (1→3)-β-D-glucan. If high levels of reactivity are not required for a particular application, longer heating times can be tolerated. In various embodiments, the LAL heating time is optionally no more than $t_B$ hours, where $t_B = K * 0.177 * 2.718^{(76510/(T+273))}/(2.20*10^{103})$, where K is 10.0, 9.5, 9.0, 8.5, 8.0, 7.5, 7.0, 6.5, 6.0, 5.5, 5.0, 4.5, 4.0, 3.5, 3.0, 2.5, 2.0, 1.5, 1.0 or less, depending on the tolerance for inactivation of (1→3)-β-D-glucan reactivity.

After heating according to any of the methods described above, any precipitate is removed from the lysate, such as by centrifugation. The lysate can also be prepared for use or storage, for example by admixing one or more additives (such as salts and/or buffer), or by lyophilization. Preferably, neither endotoxin neutralizing peptides nor anti-Factor C antibodies are added, as these can add complexity and cost to the process of preparing the heat-treated LAL.

In another aspect, the invention provides a heat-treated LAL comprising (1→3)-β-D-glucan-sensitive *Limulus* Factor G. The LAL has an endotoxin reactivity less than 0.1% of the endotoxin reactivity of an untreated *Limulus* amebocyte lysate. The LAL may be lyophilized, and preferably remains sensitive to 100 pg/mL, 10 pg/mL, 1 pg/mL, or even 0.1 pg/mL of carboxymethylated pachyman, while preferably being insensitive to 200 EU/mL of Reference Standard Endotoxin, and/or to 0.01, 0.1, 1, or even 10 mcg/mL of lipopolysaccharide (LPS).

To facilitate the detection of a (1→3)-β-D-glucan, the invention also provides a composition including a heat-treated *Limulus* amebocyte lysate and a substrate which, upon activation of the LAL, yields a detectable product indicative of the activation of the lysate. The substrate may, for example, be chromogenic, presenting a change in absorbance at a particular wavelength or spectrum of wavelengths upon activation of the lysate. Alternatively, the substrate may be fluorogenic, with fluorescent properties that change (increasing or decreasing or changing wavelength, for example) upon activation of the lysate.

The invention also provides methods for detecting a (1→3)-β-D-glucan in a sample. The methods include combining the sample with a substrate and a heat-treated *Limulus* amebocyte lysate according to any of the above descriptions. The methods can include detecting a change in an optical property (such as absorbance, transmittance, fluorescence or turbidity) of the sample after the combination with the substrate and heat-treated LAL.

The invention will be further understood in view of the drawing, specification, and claims which follow.

DETAILED DESCRIPTION OF THE INVENTION

The present invention provides a method for preparing *Limulus* amebocyte lysates with enhanced specificity for (1→3)-β-D-glucan and reduced sensitivity to endotoxin. This objective is achieved without the need for additives such as endotoxin neutralizing peptides or antibodies, and without the need for exposure to chromatographic media. In this way, unnecessary expense and labor are avoided. Perhaps more importantly, unnecessary exposure of the LAL to potential sources of contamination is also avoided. The present invention provides a simple, controlled heating step, which can be done on a crude lysate sealed, for example, in a vial or tube, creating little opportunity for contamination. The LAL can subsequently be centrifuged to remove any precipitate and lyophilized for storage and later use in a β-glucan detection assay.

As used herein, the term, "(1→3)-β-D-glucan" is understood to mean any polysaccharide or derivative thereof that is (i) capable of inducing formation of a coagulin clot in Limulus amebocyte lysate, and (ii) contains β-D glucosides, connected by a (1→3)-β-D glycosidic linkage. It is contemplated that such a polysaccharide or derivative thereof, in addition to containing a (1→3)-β-D glycosidic linkage, may also contain glucoside moieties connected by a variety of other glycosidic linkages, for example, via a (1→4)-β-D glycosidic linkage and/or by a (1→6)-β-D glycosidic linkage. It is contemplated that such (1→3)-β-D-glucans may be isolated from a variety of sources including, without limitation, plants, bacteria, yeast, algae, and fungi, or alternatively may be synthesized using conventional sugar chemistries.

As used herein, Limulus amebocyte lysate, or LAL, can include a complete amebocyte lysate from Limulus polyphemus, or a fraction or component thereof, naturally derived or recombinantly produced, containing Limulus polyphemus Factor G and detectably reactive with a (1→3)-β-D-glucan.

Heat-Treatment of LAL

The LAL is generally heated while in a sealed container (for example, a sealed tube or vial) to minimize the risk of contamination. The heat can be applied in any controlled manner, such as immersion in a temperature-controlled water bath or heating block. For shorter heating times, heating conditions can be selected to minimize the differential between the temperature of the environment and the temperature of the LAL by, for example, using a sealed container with thinner and/or more heat-conductive walls, reducing the volume of LAL, or using a container with a larger ratio of surface area/unit volume (such as a flatter container, a coiled container, etc.)

The LAL is heated to a temperature exceeding 40'C. As shown in Tables 1 and 2 of Example 2 (in which increases in onset time are a measure of decreases in reactivity), at 40° C., endotoxin reactivity is slightly reduced after 30 minutes, whereas β-glucan reactivity remains essentially unaffected. In contrast, at 47° C., endotoxin reactivity is largely eliminated after only 20 minutes, whereas β-glucan reactivity is only slightly reduced. Thus, across a range of temperatures endotoxin reactivity decreases more rapidly than β-glucan reactivity, permitting a controlled reduction in endotoxin reactivity while preserving β-glucan reactivity. As the required sensitivity to β-glucan will vary (for example, based on whether the detection is for clinical or industrial purposes), the temperature and heating time can be selected to preserve a desired level of β-glucan reactivity and/or to eliminate a desired fraction of endotoxin reactivity. Although a range of temperatures can be used, higher temperatures necessitate significantly shorter heating times. For example, at temperatures above 56° C. the heating time is preferably less than one minute (and, for increasingly elevated temperatures, substantially less than one minute).

Accordingly, temperatures greater than 40° C. but less than 56° C. can be more convenient. On the other hand, as inactivation of endotoxin reactivity is comparatively slow 40° C.-45° C., often requiring in excess of forty minutes to achieve substantial inactivation of endotoxin reactivity, temperatures greater than 45° C. (for example, 45° C.-55° C., 45° C.-52° C., or 45° C.-50° C.) can provide a more efficient process for preparing a (1→3)-β-D-glucan-specific LAL.

Typically the methods involve heating the LAL to between 40° C. and 80° C., although at higher temperatures (particularly at or above 56° C.), heating times should be correspondingly brief to avoid also rendering the LAL insensitive to (1→3)-β-D-glucan. For example, at temperatures above 56° C. the heating time is preferably less than one minute. In contrast, depending on the desired degree of reduction in endotoxin reactivity, if the temperature is no more than 45° C., heating times exceeding 40 minutes may be used.

In certain embodiments, the LAL is heated to a maximum temperature above 40° C. but no more than 45° C. (for example, 41° C.-45° C., 42° C.-45° C., 43° C.-45° C., 44° C.-45° C., or about 45° C.). In certain embodiments, the LAL is heated to a temperature above 45° C. (for example, 46° C.-80° C., 46° C.-70° C., 46° C.-60° C., 46° C.-55° C., 46° C.-54° C., 46° C.-53° C., 46° C.-52° C., 46° C.-51° C., 46° C.-50° C., 46° C.-49° C., 46° C.-48° C., 46° C.-47° C., or about 46° C.). Heating to temperatures less than 55° C. (for example, 41° C.-55° C., 41° C.-54° C., 41° C.-53° C., 41° C.-52° C., 41° C.-51° C., 41° C.-50° C., 41° C.-49° C., 41° C.-48° C., 41° C.-47° C., 41° C.-46° C.) or less than 53° C. (for example, 42° C.-53° C., 43° C.-53° C., 44° C.-53° C., 45° C.-53° C., 46° C.-53° C., 47° C.-53° C., 48° C.-53° C., 49° C.-53° C., 50° C.-53° C., 51° C.-53° C., or 52° C.-53° C.) provides the advantage of a slower degradation of (1→3)-β-D-glucan reactivity.

The heating time of the LAL can be varied depending on the temperature and the desired level of endotoxin and (1→3)-β-D-glucan reactivities. For example, the heating time can be less than one minute; 1-5 minutes; 1-10 minutes; 1-20 minutes; 1-30 minutes, 1-40 minutes; 1-50 minutes; 1-60 minutes; 1-80 minutes; 1-100 minutes; 1-120 minutes; 1-240 minutes; at least five minutes; 5-10 minutes; 5-20 minutes; 5-30 minutes; 5-40 minutes; 5-50 minutes; 5-60 minutes; 5-80 minutes; 5-100 minutes; 5-120 minutes; 5-240 minutes, at least twenty minutes, 20-30 minutes; 20-40 minutes; 20-50 minutes; 20-60 minutes; 20-80 minutes; 20-100 minutes; 20-120 minutes; 20-240 minutes; more than forty minutes; 40-50 minutes; 40-60 minutes; 40-80 minutes; 40-100 minutes; 40-120 minutes; 40-240 minutes; two hours or less; or, at the lower temperatures, as long as several days.

In certain embodiments the lysate is tested to 40° C. for 750-13500 minutes, or to 41° C. for 425-6200 minutes, or to 42° C. for 240-2900 minutes, or to 43° C. for 137-1350 minutes, or to 44° C. for 78-620 minutes, or to 45° C. for 45-290 minutes, or to 46° C. for 26-135 minutes, or to 47° C. for 15-64 minutes, or to 48° C. for 8.5-31 minutes, or to 49° C. for 5-15 minutes, or to 50° C. for 2.5-7 minutes, or to 51° C. for 1.5-3.5 minutes, or to 52° C. for 1-1.6 minutes, or to 53° C. for 0.6-0.8 minutes.

As seen in the following Tables, the rate of inactivation of endotoxin reactivity varies dramatically based on the incubation temperature. Indeed, both the rate of inactivation of endotoxin reactivity and the rate of inactivation of β-glucan reactivity increase exponentially with increasing temperature. An analysis of the relationships among heating time, temperature, and rates of inactivation of endotoxin reactivity and β-glucan reactivity is provided in Example 8. As discussed in Example 8, a series of experiments measured onset times for activation of heat-treated LAL. The experiments varied heating time, temperature, and concentration of endotoxin or β-glucan. The observed result for the reagents used was that the heating time required to achieve a 1,000-fold reduction in endotoxin reactivity was $t_{A1}$ hours, where $t_{A1}=0.825*2.718^{(56340/(T+273))}/(9.54*10^{76})$, where T is the temperature in ° C. Achieving a 1,000,000-fold reduction would require twice as long: $t_{A2}$ hours, where $t_{A2}=1.65*2.718^{(56340/(T+273))}/(9.54*10^{76})$. The desired, required or permitted retention of endotoxin reactivity may vary from one application to another (as it varies, for example, between industrial and diagnostic applications). Thus, more generally, a target heating time may be greater than or equal to $t_A$ hours, where $t_A=K*0.275*2.718^{(56340/(T+273))}/(9.54*10^{76})$; K may be, for example, 0.5, 1.0, 1.5, 2.0, 2.5, 3.0, 3.5, 4.0, 4.5, 5.0, 5.5, 6.0, 6.5, 7.0, 7.5, 8.0, or more, depending on the desired magnitude of endotoxin reactivity inactivation.

Similarly, the rate of reduction of β-glucan reactivity increases exponentially with increasing temperature, although with moderate heating temperatures the rate of loss for β-glucan reactivity can be substantially smaller than the rate of loss for endotoxin reactivity. Thus, the observed result in Example 8 was that the heating time that leads to a 10-fold loss of β-glucan reactivity was $t_{B1}$ hours, where $t_{B1}=0.353*2.718^{(76510/(T+273))}/(2.20*10^{103})$, where T is the temperature in ° C. Again, because in various applications the tolerance for loss of β-glucan reactivity may vary, a target heating time may be less than or equal to $t_B$ hours, where $t_B=K*0.177*2.718^{(76510/(T+273))}/(2.20*10^{103})$, where K is 10.0, 9.5, 9.0, 8.5, 8.0, 7.5, 7.0, 6.5, 6.0, 5.5, 5.0, 4.5, 4.0, 3.5, 3.0, 2.5, 2.0, 1.5, 1.0 or less.

Following heat treatment, any precipitate can be removed from the lysate by centrifugation (at 2500×G for 20 minutes, for example), filtration, or other separation step.

The heat-treated LAL can also be dried onto a solid surface (such as a vial, a cartridge or a 12-well or 96-well plate), such as by lyophilization. Prior to drying, one or more additives are optionally admixed with the heat-treated LAL. For example, a resolubilizing and/or an anti-flaking agent can be included. The resolubilizing agent is an agent that, either alone or in combination with another resolubilizing agent, facilitates the resolubilization of one or more components of the LAL once the LAL is exposed to a fluid sample. The resolubilizing agent preferably also stabilizes the lysate in its dried form. The resolubilizing agent provided in the mixture facilitates the stability of the reagents and their dissolution during the assay. Resolubilizing agents include, for example, one or more sugars, salts, or combinations thereof. Preferred sugar resolubilizing agents include, for example, mannitol, mannose, sorbitol, trehalose, maltose, dextrose, sucrose, and other monosaccharides or disaccharides. The anti-flaking agent included in the mixture further stabilizes the reagents and reduces flaking of the dried lysate. The anti-flaking agent preferably also stabilizes the lysate in its dried form. Preferred anti-flaking agents include, for example, one or more polymers, for example, polyethylene glycol, polyvinyl pyrolidone, polyvinyl alcohol, mannitol, dextran, and proteins, for example, serum albumin. An anti-frothing agent such as polyvinyl alcohol or polypropylene glycol can also be included. Salts and/or buffers, such as sodium chloride, magnesium sulfate, and HEPES buffer can also be included, as exemplified in Example 1. Other kinds of buffers, such as TRIS-HCl buffer, TES, MOPS, PIPES, BES, MOPSO, DIPSO, MOBS, TAPSO, HEPPSO, POPSO, TEA, EPPS, Tricine, and phosphate can be used, as can other buffers with buffering capacity between pH 7 and pH 8, as this is a preferred range of pH for the reaction. The target pH of the composition, after admixture with a sample, is preferably between 7.3 and 8.0.

The mixture can be dried onto a surface of the conduit in an environment having a temperature of about 4° C. to about 40° C., more preferably, from about 10° C. to about 35° C., more preferably, from about 15° C. to about 30° C. and a relative humidity of about 0% to about 30%, more preferably, from about 2% to about 20%, more preferably, from about 4% to about 10%. Preferably, the temperature is about 25° C. and the relative humidity is about 5%. Drying preferably occurs for about 10 minutes to about 8 hours, more preferably for about 1 hour in a temperature regulated drying chamber.

In another embodiment, the mixture is dried onto the surface of the conduit by lyophilization or freeze-drying, for example, at temperatures below 0° C., for example, from about −75° C. to about −10° C., more preferably from about −30° C. to about −20° C.

β-Glucan Assays

Heat-treated LAL can be used to detect β-glucan using any of a variety of endpoint or kinetic assays. Exemplary endpoint assays include an endpoint chromogenic assay or an endpoint turbidimetric assay. Exemplary kinetic assays include a kinetic turbidimetric assay, a one-step kinetic assay or a multi-step kinetic assay. Each of the assays is discussed in more detail below. Furthermore, it is understood that the assays may be modified to be performed in a particular assay format, for example, in a cartridge or in the well of a plate, for example, a 96 well plate.

(1) Kinetic Assays

Exemplary kinetic assays include multi-step kinetic assays, single-step kinetic assays, and kinetic turbidimetric assays.

(i) Multi-Step Kinetic Assay

A multi-step kinetic assay (for example, as described in U.S. Pat. No. 7,329,538) is initiated by combining the sample to be tested with a volume of heat-treated LAL to produce a sample-LAL mixture. The mixture then is incubated for a predetermined period of time. The mixture then is contacted with a substrate, for example, a chromogenic or fluorogenic substrate, to produce a sample-LAL-substrate mixture. Thereafter, the time in which a preselected change in an optical property (for example, a specific change in an absorbance value or a specific change in a transmission value) is measured.

The assay can be calibrated by measuring the time in which a preselected change in an optical property occurs when a certain amount of carboxymethylated pachyman or other β-glucan is introduced into the assay. By comparing the result generated by a test sample against the results generated by one or more known amounts of β-glucan, it is possible to detect the presence or amount of β-glucan in a test sample.

It is understood that a multi-step kinetic assay can be run in a cartridge format. The cartridge preferably is used with an optical detector, for example, a hand-held optical detector as shown and described in U.S. Pat. No. Des. 390,661.

By way of example and as illustrated in FIGS. 7A-7D, cartridge 1 has a substantially planar housing fabricated, for example, from a moldable biocompatible material. The housing may be fabricated from any material, however, transparent and/or translucent glass or polymers are preferred. Preferred polymers include, for example, polystyrene, polycarbonate, acrylic, polyester, optical grade polymers, or any plastic such that the optical cell is substantially transparent. The housing contains at least one fluid inlet port 4, at least one optical cell 6, and at least one conduit 8 having a fluid contacting surface for providing fluid flow communication between the fluid inlet port 4 and optical cell 6. The only requirements for the optical cell 6 are that it defines a void capable of containing a sample to be tested and that a portion of the optical cell 6 is transparent to light. Cartridge 1 may also have at least one pump port 12 in fluid flow communication with fluid inlet port 4 and optical cell 6 for attaching the cartridge 1 to a pump. The pump may then impart a negative pressure via pump port 12 to pull the sample from fluid inlet port 4 to optical cell 6. A heat-treated LAL is disposed on a first region 14 of the fluid contacting surface of conduit 8, so that when a sample is applied to fluid inlet port 4, the sample traverses region 14 and solubilizes or reconstitutes the LAL into the sample as it moves toward optical cell 6.

A second region 16 of the fluid contacting surface of conduit 8 is spaced apart from and downstream of first region 14. In this configuration, LAL is disposed at first region 14 and a chromogenic or fluorogenic substrate is disposed at second region 16, so that after the sample is contacted with the LAL in region 14, the sample-lysate mixture traverses conduit 8 and contacts the substrate in region 16. The sample-lysate-substrate mixture then traverses conduit 8 to optical cell 6.

The cartridges can be designed and used according to the type and/or number of tests required. For example, a single sample may be tested, for example, in duplicate or triplicate, for example, for research laboratory use or for medical device and biopharmaceutical testing. Alternatively, two or more different samples may be tested individually. The cartridge preferably is a single-use, disposable cartridge that is discarded after one use. The cartridges typically use approximately 20-100 fold less hemocyte lysate per sample than is used in the conventional endpoint chromogenic or kinetic chromogenic assays performed in multi-well plates, and thus provides a less costly and environmentally-friendlier test.

Figure 7A:
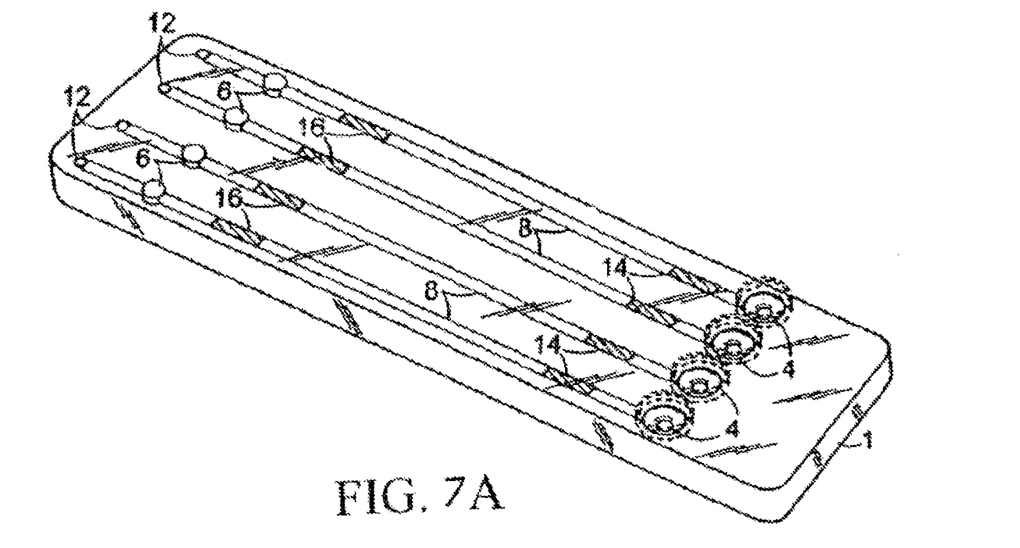
FIGS. 7A-7D are schematic illustrations in perspective view (FIG. 7A), top view (FIG. 7B), side view (FIG. 7C), and end view (FIG. 7D), of an exemplary cartridge useful in performing β-glucan assays with the heat-treated LAL of the present invention.
Figure 7B:
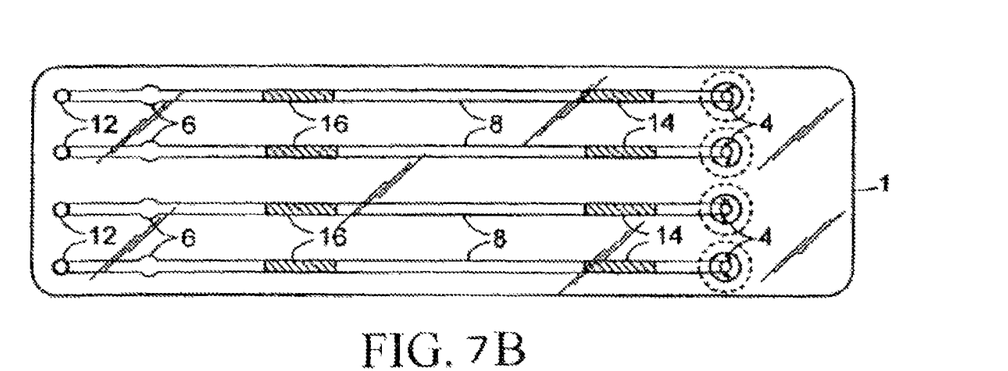
Figure 7C:
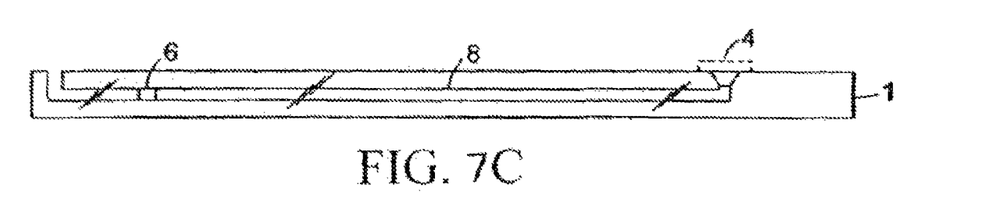
Figure 7D:
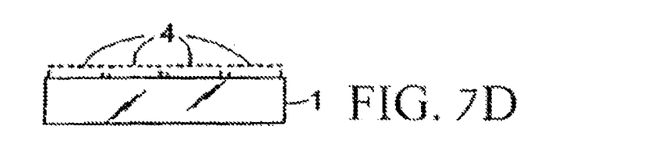

With reference to FIG. 7A, in order to perform a multi-step kinetic assay in a exemplary cartridge 1, a sample is first moved, for example, by pump action, to a first region 14 containing the heat-treated LAL, where it is mixed and incubated for a predetermined period of time. The sample-LAL mixture then is moved, for example, by pump action, to the second region 16 containing the substrate, for example, a chromogenic or fluorogenic substrate, where it is solubilized. The sample-substrate mixture then is moved to optical cell 6, for a measurement of an optical property. The time intervals required for mixing and incubating steps are preprogrammed for optimal specificity and sensitivity to the β-glucan concentration range of interest.

Although the multi-step assay may be performed in a cartridge of the type discussed above, it may also be employed in a variety of other formats, for example, within the well of a microtiter plate. In this type of assay, a sample of interest is combined with a heat-treated LAL and incubated for a predetermined period of time. Then, after the predetermined period of time, a chromogenic or fluorogenic substrate is added to the well. After mixing, the time in which a preselected change in an optical property occurs is measured. The result can then be compared against one or more standard values to measure the presence or amount of β-glucan in the sample.

In the well-type format, the samples and reagents are added to each of the wells, preferably using an automated system, such as a robot, and the plate processed by a microplate reader, which can be programmed to sequentially read the absorbance of each well in a repetitive fashion.

(ii) Single-Step Kinetic Assay

A single-step kinetic assay, for example, a single step-chromogenic assay, is described in U.S. Pat. No. 5,310,657. Briefly, a kinetic chromogenic assay includes the steps of (i) simultaneously solubilizing a heat-treated LAL with a sample to be analyzed and a substrate, for example, a chromogenic substrate, (ii) incubating the resulting mixture at a temperature of about 0° to about 40° C., preferably about 25° to about 40° C., over a predetermined time range and (iii) measuring a time required for a calorimetric change to reach a pre-selected value or change of the calorimetric readout, using a conventional spectrophotometer.

This type of assay, like the multi-step kinetic assay, can be performed in a cartridge or a well-type format. A cartridge similar to that described above for the multi-step kinetic assay can be modified for use in single-step kinetic assay. With reference to FIG. 7A, chromogenic or fluorogenic substrate is applied, for example, to the surface of conduit 8 at first region 14 together with the heat-treated LAL. To perform a kinetic assay in cartridge 1 and in reference to FIG. 7A, a sample is moved, for example, by pump action, to a first region 14 of the conduit 8 containing both the LAL and substrate, where they are solubilized, for example, by cycling between forward and reverse pump action. The sample-LAL-substrate mixture then is moved to optical cell 6 for measurement of an optical property, for example, the absorbance or transmittance properties of the sample by an optical detector. The detector may determine how long it takes for each optical property to exhibit, for example, a 5% drop in optical transmittance. Results from multiple assays, for example, two assays, can be averaged.

The assay can be calibrated by measuring the time in which a preselected change in an optical property occurs when a certain amount of β-glucan is introduced into the assay. By comparing the result generated by a test sample against one or more results with known amounts of β-glucan, it is possible to measure the presence or amount of β-glucan in the test sample.

This type of assay format may be employed in a variety of other formats, for example, within the well of a microtiter plate. In this type of assay, a sample of interest is mixed with a heat-treated LAL and a chromogenic or fluorogenic substrate. After mixing, the time in which a preselected change in an optical property occurs is measured. The result can then be compared against standard values to measure the presence or amount of β-glucan in the sample of interest.

(iii) Kinetic Turbidimetric Assay

A kinetic turbidimetric β-glucan assay can include the steps of (i) solubilizing a heat-treated LAL with a sample to be analyzed, (ii) incubating the resulting mixture at a temperature of about 0° to about 40° C., preferably about 25° to about 40° C., over a predetermined time range, and (iii) measuring a time required for either a turbidity change caused by coagulation to reach a pre-selected value or a ratio in change of the turbidity, using a conventional coagulometer, nepherometer, or spectrophotometer.

This type of assay, like the previous assays, can be performed in a cartridge or a well-type format. A cartridge similar to that described above for the multi-step or single-step kinetic assays can be modified for use in kinetic turbidimetric assays. With reference to FIG. 7A, no chromogenic or fluorogenic substrate needs to be applied to either first region 14 or second region 16.

Referring to FIG. 7A, in order to perform a kinetic turbidimetric assay in a cartridge 1, a sample is, for example, moved to a first region 14 of the conduit 8 containing the heat-treated LAL, where it is solubilized, for example, by cycling between forward and reverse pump action. The sample-lysate mixture then is moved to optical cell 6 for measurement of an optical property, for example, turbidity, by measuring, for example, the absorbance or transmittance properties of the sample-lysate mixture using an optical detector. The detector may determine how long it takes for each optical property to exhibit, for example, a 5% drop in optical transmittance. Results from multiple assays, for example, two assays can be averaged.

The assay can be calibrated by measuring the time in which a preselected change in an optical property, for example, turbidity, occurs when a certain amount of β-glucan is introduced into the assay. By comparing the result generated by a test sample against one or more results with known amounts of β-glucan, it is possible to measure the presence or amount of β-glucan in the test sample.

This type of assay format may be employed in a variety of other formats, for example, within the well of a microtiter plate. In this type of assay, a sample of interest is mixed with a heat-treated LAL. After mixing, the time in which a preselected change in an optical property, for example, turbidity, occurs is measured. The result can then be compared against standard values to measure the presence or amount of β-glucan in the sample of interest.

(2) Endpoint Assays

Exemplary endpoint assays include endpoint chromogenic or fluorogenic and endpoint turbidimetric assays.

(i) Endpoint Chromogenic or Fluorogenic Assay

Endpoint chromogenic or fluorogenic β-glucan assays can include the steps of (i) solubilizing a heat-treated LAL with a sample to be analyzed, (ii) incubating the resulting mixture at a temperature of about 0° to about 40° C., preferably about 25° to about 40° C., for a predetermined time, (iii) contacting substrate, for example, a chromogenic or fluorogenic substrate, with the incubated sample-LAL mixture, (iv) optionally adding a reaction inhibitor, for example, acetic acid, and (v) measuring, for example by calorimetric change, a substance produced from the substrate by enzymatic activity.

This type of assay can be performed in a cartridge or in a well-type format. When an endpoint chromogenic or fluorogenic assay is performed in a cartridge 1 (see, FIG. 7A), a sample is moved, for example, to a first region 14 of the conduit 8 containing the heat-treated LAL, where it is solubilized, for example, by cycling between forward and reverse pump action. Following a predetermined incubation period, the sample-LAL mixture then is moved, for example, by pump action to a second region 16 of the conduit 8 containing the chromogenic or fluorogenic substrate, where it is solubilized, for example, by cycling between forward and reverse pump action. The sample-LAL-substrate mixture optionally then is moved to a third region containing a reaction inhibitor. Afterwards, the sample-LAL-substrate mixture is moved to optical cell 6 for measurement of an optical property, for example, the absorbance or transmittance properties of the sample by an optical detector. It is contemplated, however, that when performing an end-point chromogenic or fluorogenic assay in a cartridge it is not necessary to stop the reaction using a reaction inhibitor. Under this type of assay, the final optical readings (endpoint readings) are recorded at a predetermined time.

The assay can be calibrated by measuring an optical property, for example, absorbance or transmittance, when a certain amount of β-glucan is introduced into the assay. By comparing the result generated by a test sample against one or more results with known amounts of β-glucan, it is possible to measure the presence or amount of β-glucan in the test sample.

As discussed, this type of assay format may be employed in a variety of other formats, for example, within the well of a microtiter plate. In this type of assay, a sample of interest is mixed with a heat-treated LAL and incubated for a preselected period of time. Then, a chromogenic or fluorogenic substrate is added to the mixture and the sample incubated for another period of time. Then a reaction inhibitor, for example, acetic acid, is added to the sample, and an optical property of the sample, for example, absorbance or transmittance, is measured. The result can then be compared against standard values to measure the presence or amount of β-glucan in the sample of interest.

(ii) Endpoint Turbidimetric Assay

End point turbidimetric β-glucan assays can include the steps of (i) solubilizing a heat-treated LAL with a sample to be analyzed, (ii) incubating the resulting mixture at a temperature of about 0° to about 40° C., preferably about 25° to about 40° C., for a predetermined time, (iii) optionally adding a reaction inhibitor, for example, acetic acid, and (iv) measuring the increase in turbidity as a result of coagulation, if any, using a conventional coagulometer, nepherometer, or spectrophotometer.

Endpoint turbidimetric assays can be performed in a cartridge-type format. With reference to FIG. 7A, a sample is applied to cartridge 1 and is moved, for example, to a first region 14 of the conduit 8 containing the hemocyte lysate, where it is solubilized, for example, by cycling between forward and reverse pump action. The sample-lysate mixture then is moved to optical cell 6 for measurement of an optical property, for example, turbidity, using an optical detector. Results from multiple assays, for example, two assays can be averaged.

The assay can be calibrated, for example, by measuring the turbidity at a preselected time when a certain amount of β-glucan is introduced into the assay. By comparing the result generated by a test sample against one or more results with known amounts of β-glucan, it is possible to measure the presence or amount of β-glucan in the test sample.

This type of assay format may also be run in other formats, for example, within the well of a microtiter plate. In this type of assay, a sample of interest is mixed with a heat-treated LAL and incubated for a preselected period of time. The reaction can then be stopped by the addition of an inhibitor. An optical property, for example, turbidity, of the sample then is measured at a preselected time point. The result can then be compared against standard values to measure the presence or amount of β-glucan in the sample of interest.

Endotoxin Detection

Heat-treatment of a lysate can also be performed to reduce the differential sensitivity of the lysate to endotoxin and β-glucan. In this way, the relative reactivity of the lysate to endotoxin and to β-glucan can be titrated to provide a dual-specificity detection reagent.

Assays for endotoxin can be performed using any of the assay formats described above in the context of β-glucan assays, except that the positive control would be an endotoxin source, such as a lipopolysaccharide preparation. Such an assay can be used to confirm the specificity of a β-glucan-specific heat-treated lysate, or to detect endotoxin in a test sample using a lysate retaining sufficient sensitivity to endotoxin.

Specimen Collection and Preparation Considerations

In general, materials used to harvest, store, or otherwise contact a sample to be tested, as well as test reagents, should be free of microbial contamination, for example, should be pyrogen-free. Materials may be rendered pyrogen-free by, for example, heating at 250° C. for 30 minutes. Appropriate precautions should be taken to protect depyrogenated materials from subsequent environmental contamination.

The heat-treated LAL may be used to measure the presence or amount of β-glucan in a sample of interest, for example, in a fluid, for example, a fluid to be administered locally or systemically, for example, parenterally to a mammal, or a body fluid to be tested for infection, including, for example, blood, lymph, urine, serum, plasma, ascites fluid, lung aspirants, and the like. In addition, the assays may be used to detect β-glucan present on a surface. For example, the surface of interest is swabbed and the swab then is introduced into or dissolved in liquid. The liquid can then be assayed as described herein.

Example 1. Reactivity of Crude LAL with Endotoxin and β-Glucan

Crude LAL was prepared by harvesting hemolymph from American horseshoe crabs (*Limulus polyphemus*). The resulting hemolymph was centrifuged at 150 G for 15 minutes to collect amebocytes. The amebocytes were rinsed with 3% sodium chloride and recentrifuged at 150 G for 15 minutes. After second rinsing with 3% sodium chloride and harvesting steps by the centrifugation at 150 G for 15 minutes, the resulting amebocytes were lysed by osmotic shock with addition of water for injection, and resulting crude LAL stored at 2-8° C. until further use.

LAL for the measurement was prepared by adding 0.34 M sodium chloride, 0.04 M magnesium sulfate, 0.35% (w/v) dextran, and 0.04 M HEPES buffer (pH 8.0) to 20% (v/v) crude LAL. Carboxymethylated pachyman (CM-Pachyman, Megazyme Lot90501) as a β-glucan and Lipopolysaccharide (endotoxin) derived from *E. coli* O55:B5 (List Biological Lab, Inc., lot 20315A5) were dissolved and diluted with water for irrigation (WFI, Baxter) to obtain a 10-fold dilution series. CM-Pachyman dilutions from 0.001 to 1 ng/mL and endotoxin dilutions from 1 to 1000 ng/mL were measured.

After 0.05 mL of each of the samples were distributed in the wells of a microplate (Charles River), 0.05 mL of LAL was added to each well. Thereafter, 0.01 mL of 5 mM of a chromogenic substrate (Ac-Ile-Glu-Gly-Arg-pNA.HCl) was added to each well. The microplate was set on a microplate reader (ELx 808, BIO-TEK INSTRUMENT, Inc.), and the measurement was started. Measurements were performed at 37° C.: the absorbance of each well at 405 nm was monitored and the onset times were determined.

Figure 1:
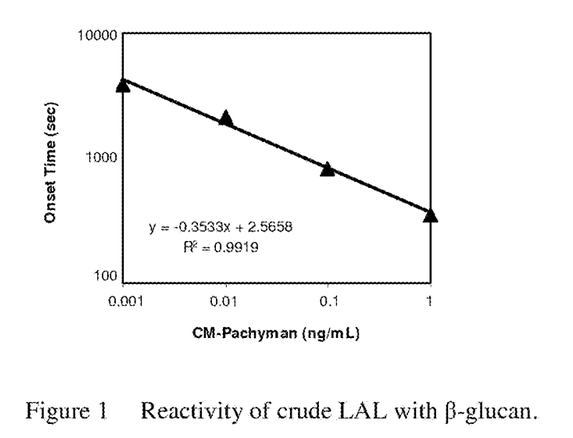
FIG. 1 is a graphical depiction of the relationship between onset time and carboxymethylated pachyman concentration for an untreated LAL.
Figure 2:
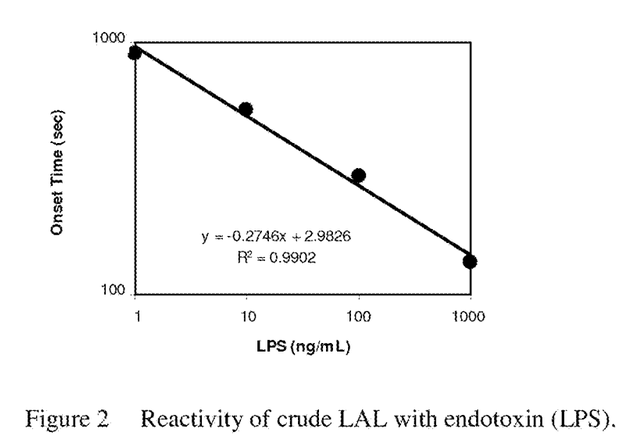
FIG. 2 is a graphical depiction of the relationship between onset time and endotoxin concentration for an untreated LAL.

FIGS. 1 and 2 show the dose-response curves of CM-Pachyman (a β-D-glucan) and endotoxin, respectively. Increased activation of LAL is reflected in a shorter "onset time" in kinetic LAL methods. As expected, the concentration of either endotoxin or carboxymethylated pachyman showed good correlations with onset time.

Example 2. Effects of Temperature on the Inactivation of the Endotoxin and β-Glucan Cascades Each 1 mL of the crude LAL prepared as described in Example 1 was distributed in depyrogenated 13 mm glass tubes. The glass tubes were incubated on an aluminum block heater at a temperature between 40° C. and 50° C. A glass tube was sampled at the scheduled incubation time, and was stored in a refrigerator. The glass tubes were centrifuged at 170 G for 20 minutes with a refrigerated centrifuge. The supernatant in the glass tubes was used as heat-treated crude LAL.

LAL for use in the assay was prepared as described in Example 1 by using the sampled crude LAL. A solution of 50 ng/mL endotoxin derived from *E. coli* O55:B5, and a solution of 100 ng/mL carboxymethlated curdlan (CM-curdlan, Wako Chemicals) (a β-D-glucan) were measured with LAL. Onset times were measured as described in Example 1. The results are summarized in Tables 1 and 2.

TABLE 1

Effect of Temperature on the Reactivity of LAL with Endotoxin.

| Incubation time | Onset time (sec) | | | | |
|---|---|---|---|---|---|
| (min) | 40° C. | 43° C. | 45° C. | 47° C. | 50° C. |
| 0 | 245 | 245 | 373 | 167 | 245 |
| 5 | not done | not done | not done | not done | 2751 |
| 10 | 339 | not done | 680 | 812 | >3600 |
| 20 | 345 | 423 | 905 | >3600 | >3600 |
| 30 | 350 | not done | 1323 | >3600 | >3600 |

TABLE 2

Effect of Temperature on the Reactivity of LAL with β-glucan.

| Incubation time | Onset time (sec) | | | | |
|---|---|---|---|---|---|
| (min) | 40° C. | 43° C. | 45° C. | 47° C. | 50° C. |
| 0 | 343 | 343 | 367 | 409 | 343 |
| 5 | not done | not done | not done | not done | 439 |
| 10 | 296 | not done | 310 | 326 | 1367 |
| 20 | 282 | 300 | 319 | 406 | >3600 |
| 30 | 276 | not done | 329 | 502 | >3600 |

Table 1 shows the effect of temperature on reactivity of the crude LAL with endotoxin. Higher temperature showed a faster decrease in reactivity of the crude LAL with endotoxin. Table 2 shows the effect of temperature on reactivity of the crude LAL with β-glucan. The β-glucan reactivity of the crude LAL was relatively more stable with increasing temperature than the endotoxin reactivity was. These data indicate that an LAL reagent for measuring β-glucan without significant reactivity with endotoxin can be prepared by using the difference in the rates of inactivation of endotoxin reactivity and β-glucan reactivity.

Example 3. Effect of Heating on Dose-Response Curves of Endotoxin and β-Glucan

Each 5 mL of the crude LAL prepared as described in Example 1 was distributed in depyrogenated 10-mL glass vials. The glass vials were incubated on an aluminum block heater at 47° C. A glass vial was sampled at the scheduled incubation time, and was stored in a refrigerator. The crude LAL in the vials was transferred to polypropylene centrifuge tubes, and the centrifuge tubes were centrifuged at 2500 G for 20 minutes with a refrigerated centrifuge. Supernatant in the centrifuge tubes was used as heat-treated crude LAL.

LAL for use in the assay was prepared as described in Example 1 by using the sampled crude LAL. A dilution series of endotoxin derived from *E. coli* O55:B5 between 10 ng/mL and 10,000 ng/mL, and a dilution series of CM-Pachyman between 1 pg/mL and 1000 pg/mL were measured with LAL. The procedures of the measurement were the same as described in Example 1. The results are summarized in FIGS. 3 and 4.

Figure 3:
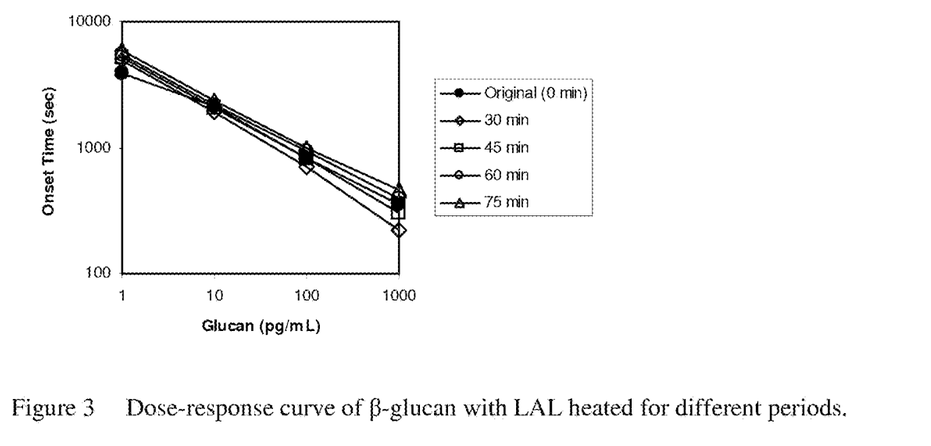
FIG. 3 is a graphical depiction of the relationship between onset time and carboxymethylated curdlan concentration for an untreated LAL or LAL heated to 47° C. for 30, 45, 60, or 75 minutes.
Figure 4:
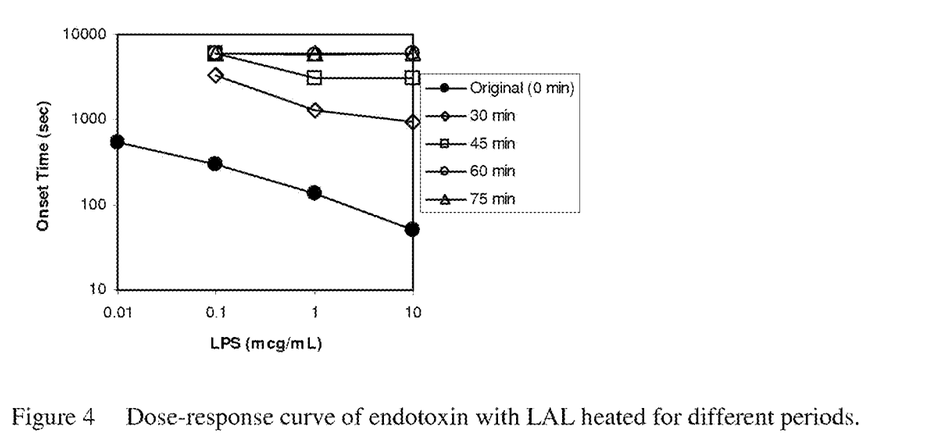
FIG. 4 is a graphical depiction of the relationship between onset time and endotoxin concentration for an untreated LAL or LAL heated to 47° C. for 30, 45, 60, or 75 minutes.

FIGS. 3 and 4 show the effect of heating on dose-response curves of endotoxin and β-glucan (CM-Pachyman), respectively. There was no considerable difference in the dose-response curves for different incubation times (30 minutes-75 minutes). On the other hand, the dose-response of endotoxin was significantly decreased by heating at 47° C.

Example 4. Effect of Reference Standard Endotoxin on the Measurement of β-Glucan with Heat-Treated LAL Each 3 mL of the crude LAL prepared as described in Example 1 was distributed in 10 depyrogenated 13 mm glass tubes. The glass tubes were incubated on an aluminum block heater at 47° C. for 15 minutes. The heated crude LAL was collected in polypropylene centrifuge tubes, and the centrifuge tubes were centrifuged at 170 G for 20 minutes with a refrigerated centrifuge. Supernatant in the centrifuge tubes was used as heat treated crude LAL.

LAL for use in the assay was prepared as described in Example 1 by using the heated crude LAL. Dilution series of CM-Curdlan between 1 ng/mL and 100 ng/mL were prepared with and without 200 EU/mL US Reference Standard Endotoxin (RSE). The dilutions were measured with LAL. The procedures of the measurement were same as described in Example 1. The results are summarized in FIG. 5.

Figure 5:
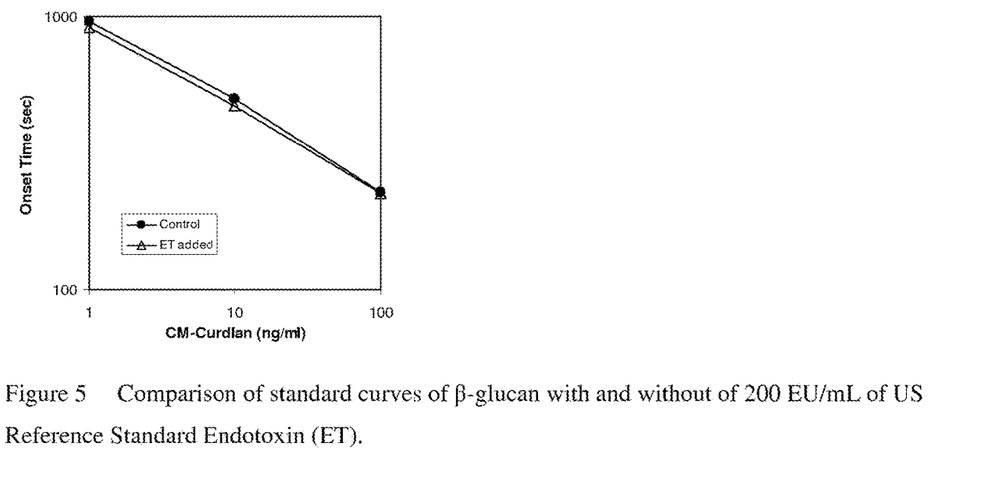
FIG. 5 is a graphical depiction comparing standard curves of carboxymethylated curdlan with and without of 200 EU/mL of US Reference Standard Endotoxin.

FIG. 5 shows the effect of RSE on the β-glucan standard curve. The standard curve was not affected by the addition of 200 EU/mL RSE. Considering that commonly measured endotoxin levels are less than 50 ELU/mL, normal endotoxin contamination does not interfere with the ability of the heat-treated LAL to accurately measure β-glucan levels.

Example 5. Effect of Endotoxin Derived from *E. coli* O55:B5 on the Measurement of β-Glucan with Heat-Treated LAL Each 3 mL of the crude LAL prepared as described in Example 1 was distributed in 10 depyrogenated 13 mm glass tubes. The glass tubes were incubated on an aluminum block heater at 47° C. for 20 minutes. The heated crude LAL was collected in polypropylene centrifuge tubes, and the centrifuge tubes were centrifuged at 170 G for 20 minutes with a refrigerated centrifuge. Supernatant in the centrifuge tubes was used as heat treated crude LAL.

LAL for use in the assay was prepared as described in Example 1 by using the heated crude LAL. Dilution series of CM-Curdlan between 1 ng/mL and 100 ng/mL were prepared with and without 500 ng/mL endotoxin derived from *E. coli* O55:B5. The dilutions were measured with LAL. The procedures of the measurement were same as described in Example 1. The results are summarized in FIG. 6.

Figure 6:
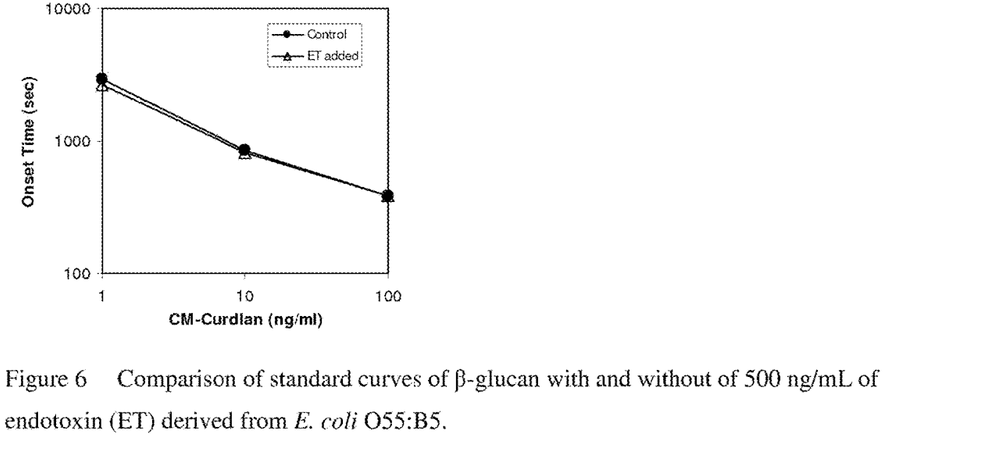
FIG. 6 is a graphical depiction comparing standard curves of carboxymethylated curdlan with and without of 500 ng/mL of endotoxin derived from *E. coli* O55:B5.

FIG. 6 shows the effect of RSE on the standard curve of β-glucan. The standard curve was not affected by the addition of 100 ng/mL endotoxin derived from *E. coli* O55:B5. Considering that 500 ng/mL endotoxin derived from *E. coli* O55:B5 approximates 5000 EU/mL, normal levels of endotoxin contamination would not interfere with the ability of the heat-treated LAL to accurately measure β-glucan levels.

Example 6. Kinetic Turbidimetric Assay with Heat-Treated LAL

Each 5 mL of the crude LAL prepared as described in Example 1 was distributed in depyrogenated 10-mL glass vials. The glass vials were incubated on an aluminum block heater at 47° C. for 60 minutes. The crude LAL in the vials was transferred to polypropylene centrifuge tubes, and the centrifuge tubes were centrifuged at 2500 G. for 20 min. with a refrigerated centrifuge. Supernatant in the centrifuge tubes was used as heat treated crude LAL.

LAL for the measurement was prepared as described in Example 1 by using the heated crude LAL. A dilution series of endotoxin derived from *E. coli* O55:B5 between 1 ng/mL and 1000 ng/mL, and a dilution series of CM-Pachyman between 1 ng/mL and 100 ng/mL were measured with LAL. The procedures of the measurement were same as described in Example 1.

Table 3 shows the reactivity of the heat treated LAL with endotoxin and β-glucan by using the kinetic turbidimetric assay (KTA). β-glucan was detected with KTA, but endotoxin did not show any reactivity even at 1000 ng/mL, again confirming the specificity of the assay for β-glucan.

TABLE 3

Reactivity of Heat Treated LAL With Endotoxin and β-glucan in a Kinetic Turbidimetric Assay.

| Concentration | Onset Time (sec) | |
|---|---|---|
| (ng/ml) | Beta-Glucan | Endotoxin |
| 1 | 3698 | >6000 |
| 10 | 1400 | >6000 |
| 100 | 1425 | >6000 |
| 1000 | Not done | >6000 |

Example 7. β-Glucan Detection in Patients

Serum samples from patients with positive blood culture were diluted 10-fold with water for injection, and the diluted serum samples were incubated at 80° C. for 10 min. The pretreated samples were measured with lyophilized heat-treated LAL by the kinetic chromogenic method. The lyophilized heat-treated LAL was prepared from the LAL described in Example 5. CM-pachyman was used as a β-glucan standard. Serum samples from healthy subjects were also pretreated and measured as the same manner.

As shown in Table 4, the β-glucan values of the serum samples from the patients were higher than 100 pg/mL, and those from the healthy subjects were less than 34 pg/mL. Since the results of blood culture of the patients showed yeast (*Candida*) and fungus (*Aspergillus*), these patients were proven as fungemia. Considering these results, the β-glucan assay with the heat-treated LAL is useful for the diagnosis of deep mycosis.

TABLE 4

β-glucan Values in Serum Samples From Fungemia Patients

| Sample | Blood culture | β-glucan (pg/mL) |
|---|---|---|
| Patient #1: Pulmonary disease | Candida albicans | 137 |
| Patient #2: Pulmonary disease | Aspergillus sp. | 878 |
| Patient# 3 | Candida albicans | 275 |
| Healthy subject #1 | not available | <34 |
| Healthy subject #2 | not available | <34 |

Figure 8:
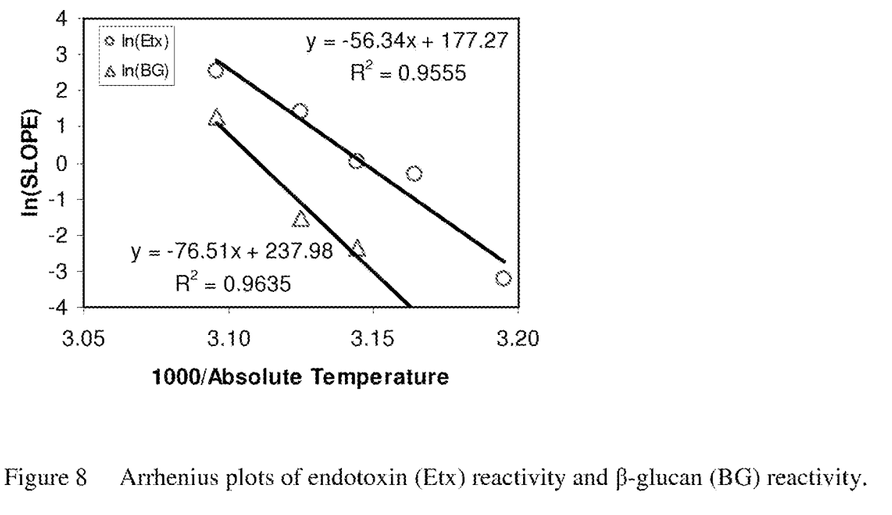
FIG. 8 is an Arrhenius plot relating the rates of lysate inactivation observed in Example 2 with absolute temperature measured in Kelvins.

Example 8. Decreases in Endotoxin and β-Glucan Reactivity as a Function of Temperature and Heating Time Analysis of the experiments described in Example 2 revealed that the rates of inactivation of endotoxin and β-glucan reactivity as a function of heating temperature have an exponential relationship that can be depicted using an Arrhenius plot. Comparing the logarithm of the onset times versus the heating times shown in Tables 1 and 2 yielded the regression parameters shown in Tables 5 and 6. Using the slopes and the temperatures, Arrhenius plots for endotoxin reactivity and β-glucan reactivity demonstrated a correlation between logarithm of the slopes and the temperature. As shown in FIG. 8, for each temperature tested, the natural log of the slope from Table 5 ("ln(Etx)") or Table 6 ("ln(BG)") was plotted against 1000/Absolute temperature (in Kelvins), yielding correlations both for rates of inactivation of endotoxin reactivity and for rates of inactivation of β-glucan reactivity.

TABLE 5

Regression Parameters of Inactivation of Endotoxin Reactivity at Several Temperatures

| Incubation time (h) | Log (onset time (sec)) | | | | |
|---|---|---|---|---|---|
| | 40° C. | 43° C. | 45° C. | 47° C. | 50° C. |
| Slope | 0.040 | 0.708 | 1.019 | 4.120 | 12.595 |
| Y-intercept | 2.524 | 2.390 | 2.613 | 2.223 | 2.390 |
| Corr. Coefficient | 0.999 | 1.000 | 1.000 | 1.000 | 1.000 |
| Temp | 40 | 43 | 45 | 47 | 50 |

TABLE 6

Regression Parameters of Inactivation of β-glucan Reactivity at Several Temperatures

| Incubation time (h) | Log (onset time (sec)) | | | | |
|---|---|---|---|---|---|
| | 40° C. | 43° C. | 45° C. | 47° C. | 50° C. |
| Slope | −0.087 | −0.175 | 0.094 | 0.217 | 3.599 |
| Y-intercept | 2.483 | 2.536 | 2.471 | 2.554 | 2.471 |
| Corr. Coefficient | −0.971 | −1.000 | 0.998 | 0.608 | 0.937 |

Based on the observed relationships between rates of inactivation and heating times and temperatures, the heating time required to achieve a certain degree of inactivation was calculated for the lysate tested in Example 2. For example, a 1,000-fold reduction in the endotoxin reactivity of the lysate of Example 2 corresponds to a heating time of $$t_{A1}=0.825*2.718^{(56340/(T+273))}/(9.54*10^{76}) \text{(hours)}.$$

A 1,000,000-fold reduction in endotoxin reactivity corresponds to a heating time twice as long:

$$t_{A2}=1.65*2.718^{(56340/(T+273))}/(9.54*10^{76}) \text{(hours)}.$$

Similarly, a 10-fold reduction in β-glucan in the lysate of Example 2 is obtained after a heating time of $$t_{B1}=1.059*2.718^{(76510/(T+273))}/(2.20*10^{103}) \text{(hours)}.$$

Because endotoxin reactivity degrades more quickly that β-glucan reactivity upon exposure to moderate heating, this permits the preparation of lysates with moderately or substantially reduced endotoxin reactivity. For example, Table 7 presents various proposed ranges of heating times and temperatures permitting, for example, an endotoxin reactivity reduction of at least 1,000-fold and/or a β-glucan reactivity reduction of no more than about 10-fold (indicated in bold-face type).

TABLE 7

| Temperature (° C.) | Heating time (minutes) | Estimated reactivity remaining | |
|---|---|---|---|
| | | Endotoxin | β-glucan |
| 40 | 750 | 0.108% | 88.0% |
| 40 | 13500 | 0.0000% | 10.1% |
| 41 | 425 | 0.105% | 85.4% |
| 41 | 6200 | 0.000% | 10.1% |
| 42 | 240 | 0.106% | 82.5% |
| 42 | 2900 | 0.000% | 9.7% |
| 43 | 137 | 0.102% | 78.9% |
| 43 | 1350 | 0.000% | 9.7% |
| 44 | 78 | 0.103% | 74.8% |
| 44 | 620 | 0.000% | 10.0% |
| 45 | 45 | 0.097% | 70.0% |
| 45 | 290 | 0.000% | 10.0% |
| 46 | 26 | 0.092% | 64.5% |
| 46 | 135 | 0.000% | 10.3% |
| 47 | 15 | 0.091% | 58.5% |
| 47 | 64 | 0.000% | 10.2% |
| 48 | 8.5 | 0.104% | 52.8% |
| 48 | 31 | 0.000% | 9.7% |
| 49 | 5 | 0.094% | 45.5% |
| 49 | 15 | 0.000% | 9.4% |
| 50 | 2.9 | 0.096% | 38.5% |
| 50 | 7 | 0.000% | 10.0% |
| 51 | 1.7 | 0.094% | 31.3% |
| 51 | 3.4 | 0.000% | 9.8% |
| 52 | 1 | 0.091% | 24.4% |
| 52 | 1.6 | 0.001% | 10.4% |
| 53 | 0.58 | 0.099% | 18.5% |
| 53 | 0.79 | 0.008% | 10.1% |
| 54 | 0.34 | 0.103% | 13.2% |
| 55 | 0.19 | 0.151% | 9.9% |
| 56 | 0.12 | 0.099% | 5.2% |
| 57 | 0.07 | 0.114% | 3.0% |
| 58 | 0.042 | 0.110% | 1.5% |
| 59 | 0.025 | 0.115% | 0.6% |
| 60 | 0.015 | 0.116% | 0.2% |

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced therein.

INCORPORATION BY REFERENCE

All publications and patent documents cited in this application are incorporated by reference in their entirety for all purposes to the same extent as if the entire contents of each individual publication or patent document was incorporated herein.

What is claimed is:

1. A heat-treated Limulus amebocyte lysate comprising:
   i) (1→3)-(β-D-glucan sensitive Limulus Factor G and
   ii) Factor C having an endotoxin reactivity less than 0.1% of the endotoxin reactivity of an untreated Limulus amebocyte lysate.

2. The Limulus amebocyte lysate of claim 1, wherein the Limulus amebocyte lysate is lyophilized.

3. The Limulus amebocyte lysate of claim 1, wherein the Limulus amebocyte lysate retains sensitivity to 1 pg/mL carboxymethylated pachyman.

4. The Limulus amebocyte lysate of claim 3, wherein the Limulus amebocyte lysate retains sensitivity to 0.1 pg/mL carboxymethylated pachyman.

5. A Limulus amebocyte lysate according to claim 1, wherein the lysate is insensitive to 200 EU/mL of Reference Standard Endotoxin.

6. A Limulus amebocyte lysate according to claim 1, wherein the lysate is insensitive to 0.01 mcg/mL LPS.

7. The Limulus amebocyte lysate of claim 6, wherein the lysate is insensitive to 0.1 mcg/mL LPS.

8. The Limulus amebocyte lysate of claim 7, wherein the lysate is insensitive to 1 mcg/mL LPS.

9. The Limulus amebocyte lysate of claim 8, wherein the lysate is insensitive to 10 mcg/mL LPS.

10. A composition comprising the heat-treated Limulus amebocyte lysate of claim 1 and a substrate.

11. The composition of claim 10, wherein the substrate is chromogenic.

12. The composition of claim 10, wherein the substrate is fluorogenic.

13. The composition of claim 10, wherein the composition is lyophilized.

14. The Limulus amebocyte lysate of claim 1, wherein the heat-treated Limulus amebocyte lysate comprises inactive Factor C.

* * * * *

UNITED STATES PATENT AND TRADEMARK OFFICE
CERTIFICATE OF CORRECTION

PATENT NO. : 11,221,335 B2
APPLICATION NO. : 16/675978
DATED : January 11, 2022
INVENTOR(S) : Tsuchiya It is certified that error appears in the above-identified patent and that said Letters Patent is hereby corrected as shown below:

In the Claims

In Claim 1 at Column 19, Line 6, replace "(1→3)-(β-D-glucan" with --(1→3)-β-D-glucan--.

Signed and Sealed this
Twentieth Day of December, 2022

Katherine Kelly Vidal
*Director of the United States Patent and Trademark Office*